United States Patent
Meister et al.

(10) Patent No.: US 9,693,155 B2
(45) Date of Patent: Jun. 27, 2017

(54) HEARING IMPLANT BILATERAL MATCHING OF ILD BASED ON MEASURED ITD

(71) Applicant: MED-EL Elektromedizinische Geraete GmbH, Innsbruck (AT)

(72) Inventors: Dirk Meister, Innsbruck (AT); Peter Schleich, Telfs (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 14/956,480

(22) Filed: Dec. 2, 2015

(65) Prior Publication Data

US 2016/0165363 A1   Jun. 9, 2016

Related U.S. Application Data

(60) Provisional application No. 62/086,897, filed on Dec. 3, 2014.

(51) Int. Cl.
*A61N 1/00* (2006.01)
*H04R 25/00* (2006.01)
(Continued)

(52) U.S. Cl.
CPC ....... *H04R 25/552* (2013.01); *A61N 1/36032* (2013.01); *A61N 1/37252* (2013.01);
(Continued)

(58) Field of Classification Search
CPC .. H04R 25/552; H04R 25/305; H04R 25/505; A61N 1/36032; A61N 1/37252
See application file for complete search history.

(56) References Cited

U.S. PATENT DOCUMENTS 8,019,429 B2   9/2011   Aschbacher et al.
8,233,629 B2   7/2012   Johnston
(Continued)

FOREIGN PATENT DOCUMENTS

WO   WO 2009/062142   5/2009
WO   WO 2009/126680   10/2009
WO   WO 2014/123890   8/2014

OTHER PUBLICATIONS

Aronoff, Justin M. et al, "The use of interaural time and level difference cues by bilateral cochlear implant users", *J. Acoust. Soc. Am.* 127 (3), Mar. 2010, 6 pages.
(Continued)

*Primary Examiner* — Scott Getzow
(74) *Attorney, Agent, or Firm* — Sunstein Kann Murphy & Timbers LLP

(57) ABSTRACT

Arrangements are described for generating electrode stimulation signals for stimulation contacts in implanted electrode arrays of a bilateral hearing implant system having electrode arrays on both the left- and right-sides. Left-side and right-side audio input signals are processed to generate corresponding left-side and right-side band pass signals, which each represent an associated band of audio frequencies in the audio input signal. Frequency-specific interaural time delays (ITDs) are estimated for the band pass signals, and the estimated ITDs are used to adjust interaural level differences (ILDs) in the band pass signals. The adjusted band pass signals then are used to generate left-side and right-side electrode stimulation signals for the stimulation contacts in the corresponding left-side and right-side electrode arrays.

20 Claims, 10 Drawing Sheets

(51) Int. Cl.
    *A61N 1/36*    (2006.01)
    *A61N 1/372*   (2006.01)
    *A61N 1/05*    (2006.01)
(52) U.S. Cl.
    CPC ......... *H04R 25/305* (2013.01); *H04R 25/505* (2013.01); *A61N 1/0541* (2013.01); *H04R 2225/023* (2013.01); *H04R 2430/03* (2013.01)

(56) References Cited

U.S. PATENT DOCUMENTS

| | | |
|---|---|---|
| 8,285,385 B2 | 10/2012 | Schleich |
| 2007/0156202 A1 | 7/2007 | Zierhofer |
| 2009/0264961 A1 | 10/2009 | Schleich et al. |
| 2010/0198300 A1* | 8/2010 | Smith .................. H04R 25/505 607/57 |
| 2012/0004706 A1 | 1/2012 | Meister et al. |
| 2013/0066626 A1 | 3/2013 | Liao |
| 2013/0094683 A1 | 4/2013 | Hansen |
| 2014/0219386 A1 | 8/2014 | Kim et al. |
| 2014/0219486 A1* | 8/2014 | Brown .................. H04R 25/43 381/320 |

OTHER PUBLICATIONS

International Searching Authority, Authorized Officer Lee W. Young, International Search Report and Written Opinion for PCT/US15/63313, date of mailing Feb. 3, 2016, 18 pages.

* cited by examiner

HEARING IMPLANT BILATERAL MATCHING OF ILD BASED ON MEASURED ITD

This application claims priority from U.S. Provisional Patent Application 62/086,897, filed Dec. 3, 2014, which is incorporated herein by reference in its entirety.

FIELD OF THE INVENTION

The present invention relates to hearing implant systems, and more specifically to signal processing arrangements in cochlear implant systems and other implantable auditory prostheses.

BACKGROUND ART

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus auditory implant systems include brainstem implants, middle brain implants, etc. each stimulating a specific auditory target in the hearing system.

FIG. 1 also shows some components of a typical cochlear implant system where an external microphone provides an audio signal input to an external implant processor 111 in which various signal processing schemes can be implemented. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed signal is then converted into a digital data format for transmission by external transmitter coil 107 into the implant stimulator 108. Besides receiving the processed audio information, the implant stimulator 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

Binaural stimulation has long been used in hearing aids, but it has only recently become common in hearing implants such as cochlear implants (CI). For cochlear implants, binaural stimulation requires a bilateral implant system with two implanted electrode arrays, one in each ear. The incoming left and right side acoustic signals are similar to those in hearing aids and may simply be the output signals of microphones located in the vicinity of the left and right ear, respectively.

FIG. 2 shows various functional blocks in a typical bilateral cochlear implant signal processing system. Independently on each side—left and right—an input sensing microphone 201 senses environmental sounds and coverts them into representative electrical signals that form audio inputs to the system. FIG. 3 shows a typical example of a short time period of an input audio signal from an input sensing microphone 201. The input audio signal is fed through multiple band pass filters (BPFs) 202 that decompose the input audio signal into multiple spectral band pass signals as shown, for example, in FIG. 4. As shown in FIG. 5, each band pass signal 501 is thought of as having a fine structure component 502 and an envelope component 503 (typically derived by Hilbert transformation). The filtered envelope signal 504 oscillates around the zero reference axis line with a frequency that is related to the fundamental frequency FO of the band pass filter.

A non-linear dynamic processing module 203 dynamically adjusts the filter envelopes by adaptive processing such as with automatic gain control (AGC) and other dynamic signal processing adjustments. Envelope detectors 204 extract the slowly-varying band pass envelope components of the band pass signals, for example, by full-wave rectification and low pass filtering. Pulse timing module 205 modulates the envelope signals with the corresponding band pass carrier waveforms to produce stimulation pulse requests on which the mapping/pulse generation module 206 performs a non-linear (e.g., logarithmic) mapping to fit the patient's perceptual characteristics and produces electrode stimulation signals in the specific form of non-overlapping biphasic output pulses for each of the stimulation contacts (EL-1 to EL-n) of each electrode array implanted in each cochlea on the left and right sides reflecting the tonotopic neural response of the cochlea.

Bilateral cochlear implants provide the benefits of two-sided hearing which can allow a listener to localize sources of sound in the horizontal plane. That requires information from both ears such as interaural level differences (ILDs) and interaural time differences (ITDs). This is discussed further, for example, in Macpherson, E. A, and Middlebrooks, J. C., *Listener Weighting Of Cues For Lateral Angle: The Duplex Theory Of Sound Localization Revisited*, J. Acoust. Soc. Am. 111, 2219-3622, 2002, which is incorporated herein by reference. An ITD is a relative time shift between signals arriving at the left and right ear which is caused by different times for the signal to reach each ear when the source of sound is not within the median plane. An ILD is a similar difference in sound levels of signals entering the ears. Two-sided hearing also is known to make speech easier to understand in noise, and again the perception of ITD plays a pivotal role therein. This is explained more fully, for example, in Bronkhorst, A. W., and Plomp, R., *The*

Effect Of Head-Induced Interaural Time And Level Differences On Speech Intelligibility In Noise, J. Acoust. Soc. Am. 83, 1508-1516, 1988, which is incorporated herein by reference.

In the perception of ITDs, two sources of ITD information can be perceived: ITD information from the signal envelope and ITD information from the signal fine structure. It has been found that the fine structure ITD information plays a more important role than the envelope ITD information for sound localization and for understanding of speech in noise. This has been shown, for example, in Wightman and Kistler, *Factors Affecting The Relative Salience Of Sound Localization Cues* in Binaural and Spatial Hearing in Real and Virtual Environments, edited by Gilkey, R. H., and Anderson, T. R., (Lawrence Erlbaum Associates, Mahwah, N.J., 1997); Smith et al., *Chimaeric Sounds Reveal Dichotomies In Auditory Perception*, in Nature 416, 87-90, 2002; Nie et al., *Encoding Frequency Modulation To Improve Cochlear Implant Performance In Noise*, IEEE Trans. Biomed. Eng. 52, 64-73, 2005; and Zeng et al., *Speech Recognition With Amplitude And Frequency Modulations*, Proc. Natl. Acad. Sci. 102, 2293-2298, 2005, all of which are incorporated herein by reference, 2005, all of which are incorporated herein by reference.

In older cochlear implant arrangements, the fine structure information was not used. Instead, the incoming sound was separated into a number of frequency bands, for each band the slowly-varying envelope was extracted, and this envelope information was used to modulate the amplitude of a high-frequency pulsatile carrier signal. In such conventional cochlear implants, the frequency and phase of the pulsatile carrier signal was simply dictated by the speech processor and not directly related to the fine structure of the incoming signal. Accordingly, with such known cochlear implants, only the envelope ITD information was available, and consequently, ITD perception was very limited.

More recent cochlear implant systems have been implemented in which the stimulation signals are comprised of stimulation pulses with a timing that is based on temporal events within the fine structure of the left and right side acoustic signals. For instance, such temporal events can be the peaks or zero crossings within the fine structure of the signal. Stimulation schemes for coding fine structure information have been described for example by U.S. Patent Publication 20040478675; U.S. Pat. No. 6,594,525; U.S. Patent Publication 2004136556; which are incorporated herein by reference, and in van Hoesel and Tyler, *Speech Perception, Localization, And Lateralization With Bilateral Cochlear Implants*, J. Acoust. Soc. Am. 113, 1617-1630, 2003; and Litvak et al., *Auditory Nerve Fiber Responses To Electric Stimulation: Modulated And Unmodulated Pulse Trains*, J. Acoust. Soc. Am. 110(1), 368-79, 2001, also incorporated herein by reference. With these improved stimulation strategies, the ITD perception should be increased as compared to stimulation strategies comprising envelope ITD information only. However, in comparative studies no improvement in sound localization or in the understanding of speech in noise environments has been found; See van Hoesel supra.

Hearing impaired listeners are also known to have difficulties with localizing sources of sound and understanding of speech in noisy environments. See for example, Colburn, S. et al. *Binaural Directional Hearing-Impairments And Aids* in W. Yost & G. Gourevitch (Eds.), Directional Hearing pp. 261-278, New York: Springer-Verlag, 1987; Durlach N. I. et al., *Binaural Interaction Of Impaired Listeners. A Review Of Past Research* in Audiology, 20(3):181-211, 1981; Gabriel K. J. et al. *Frequency Dependence Of Binaural Performance In Listeners With Impaired Binaural Hearing*, J Acoust Soc Am., January: 91(1):336-47, 1992; Hawkins D B, Wightman F L. (1980). Interaural time discrimination ability of listeners with sensorineural hearing loss. Audiology. 19, 495-507; Kinkel, M. et al., *Binaurales Hören bei Normalhörenden und Schwerhörigen I. Meßmethoden und Meßergebnisse*, Audiologische Akustik 6/91, 192-201, 1991; Koehnke, J. et al., *Effects Of Reference Interaural Time And Intensity Differences On Binaural Performance In Listeners With Normal And Impaired Hearing*, Ear and Hearing, 16, 331-353, 1995; and Smoski, W. J. and Trahiotis, C., *Discrimination Of Interaural Temporal Disparities By Normal-Hearing Listeners And Listeners With High-Frequency Sensorineural Hearing Loss*, J Acoust Soc Am. 79, 1541-7, 1986, all of which are incorporated herein by reference.

SUMMARY OF THE INVENTION

Embodiments of the present invention are directed to arrangements for generating electrode stimulation signals for stimulation contacts in implanted electrode arrays of a bilateral hearing implant system having electrode arrays on both the left- and right-sides. Left-side and right-side filter banks configured to process left- and right-side audio input to generate corresponding left-side and right-side band pass signals, which each represent an associated band of audio frequencies in the audio input signal. An ITD processing module estimates frequency-specific interaural time delays (ITDs) for the band pass signals, and uses the estimated ITDs to adjust interaural level differences (ILDs) in the band pass signals. A plurality of further audio processing stages then use the adjusted band pass signals to generate left-side and right-side electrode stimulation signals for the stimulation contacts in the corresponding left-side and right-side electrode arrays.

The ITD processing module may be configured to estimate the ITDs using one or more of the audio input signals, the band pass signals (e.g., envelope components and/or fine structure components of the band pass signals) and/or the stimulation pulse requests to estimate the ITDs. The ITD processing module may adjust channel-specific ILDs of the band pass signals and/or broadband ILDs. And the ITD processing module may adjust channel-specific dynamic components in the signals.

The ITD processing module may be configured to calculate an ITD histogram from overlapping measurement time windows to estimate the ITDs. A standard deviation of the ITD histogram may be used to characterize accuracy of the estimated ITDs and to use a function of estimation accuracy to adjust the ILDs. So for example, the ITD processing module may be configured to use an estimation accuracy threshold to determine when to adjust the ILDs such that an ILD is adjusted when estimation accuracy of the corresponding ITD is less than the estimation accuracy threshold, but the ILD is not adjusted when estimation accuracy of the corresponding ITD is greater than the estimation accuracy threshold.

DETAILED DESCRIPTION OF SPECIFIC EMBODIMENTS

Embodiments of the present invention are directed to bilateral hearing implant systems with improved use of ITD information in nonlinear/dynamic processing components that modify signal amplitudes over time and/or an ITD-to-ILD mapping stage. In broad terms, an estimate of frequency-specific ITDs is derived from one or more signal components and then used to adjust channel-specific or broadband ILDs. Dynamic signal level modifications are influenced throughout the bilateral system based on the measured ITDs.

Figure 1:
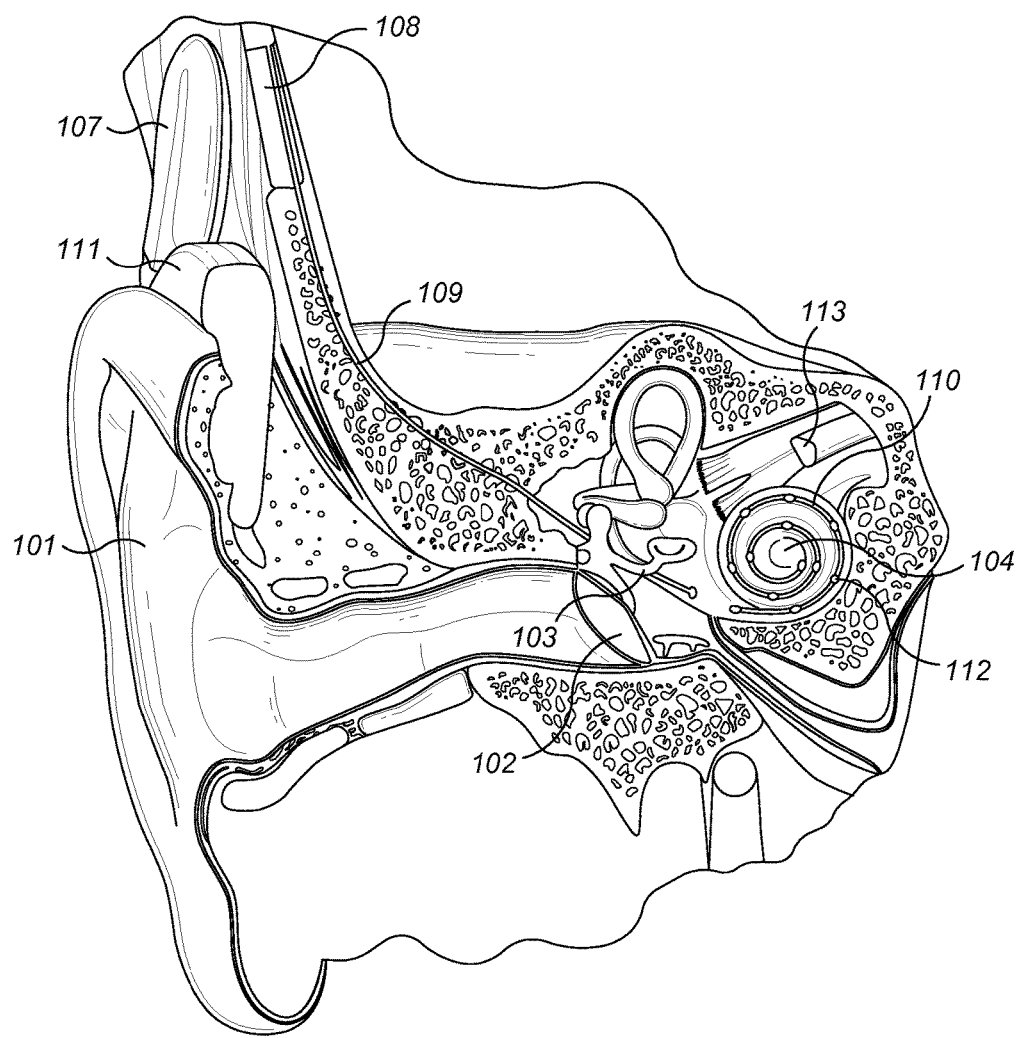
FIG. 1 shows a section view of a human ear with a typical auditory prosthesis system designed to deliver electric stimuli to the inner ear and acoustic stimuli at the ear canal.
Figure 2:
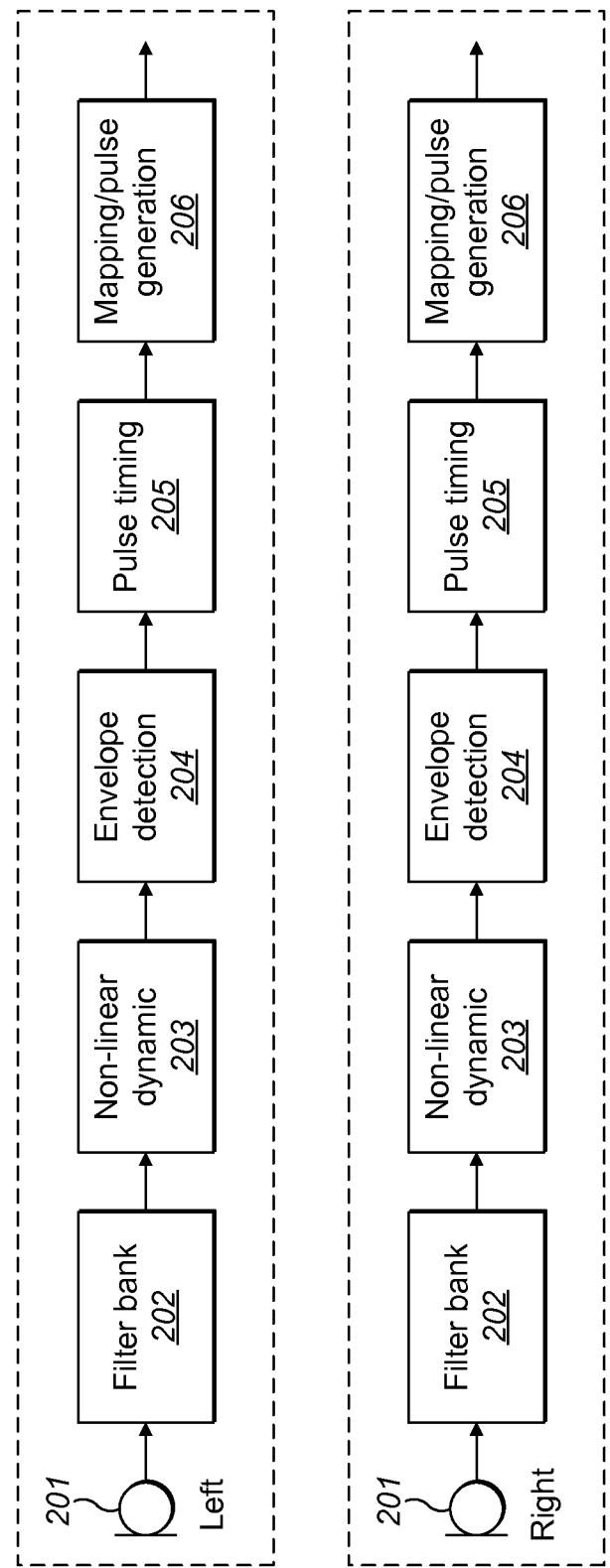
FIG. 2 shows various functional blocks in a typical bi-lateral cochlear implant signal processing arrangement.
Figure 3:
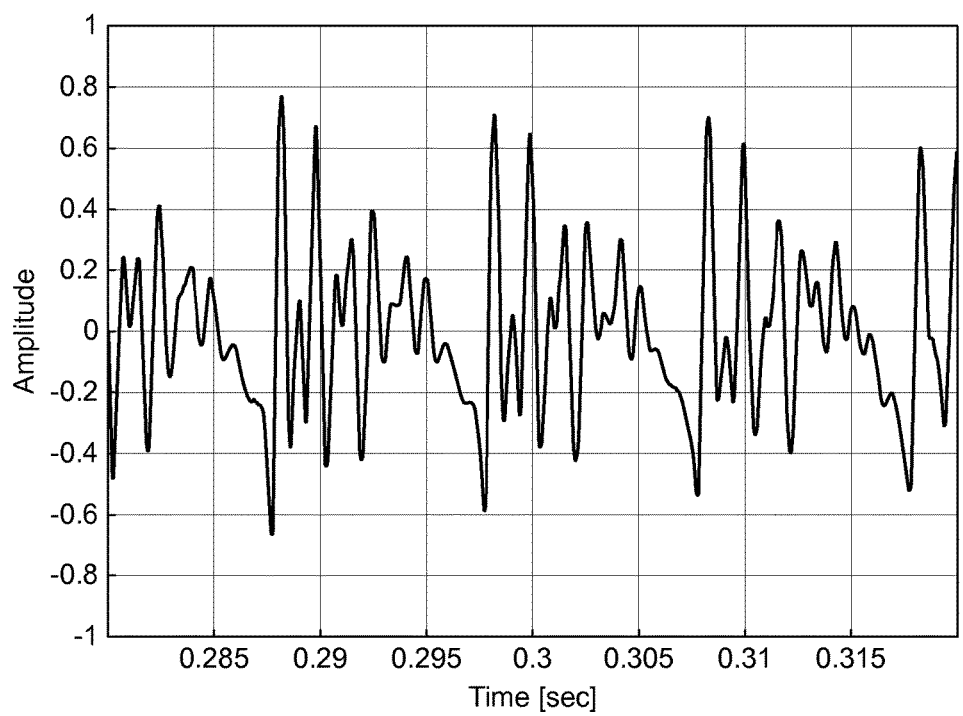
FIG. 3 shows an example of a short time period of an audio speech signal from a microphone.
Figure 4:
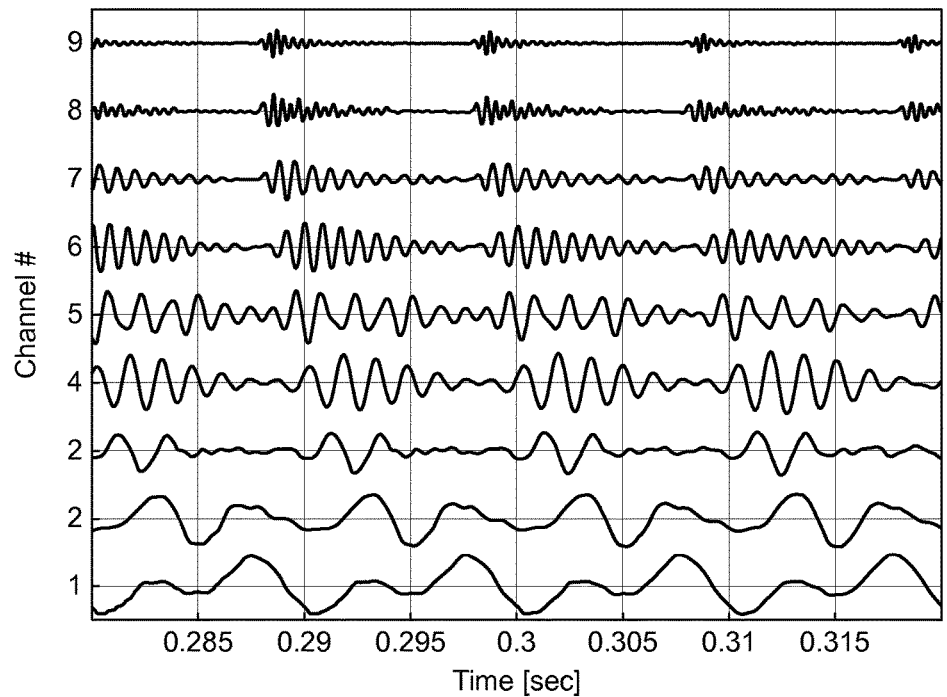
FIG. 4 shows an acoustic microphone signal decomposed by band-pass filtering by a bank of filters into a set of signals.
Figure 5:
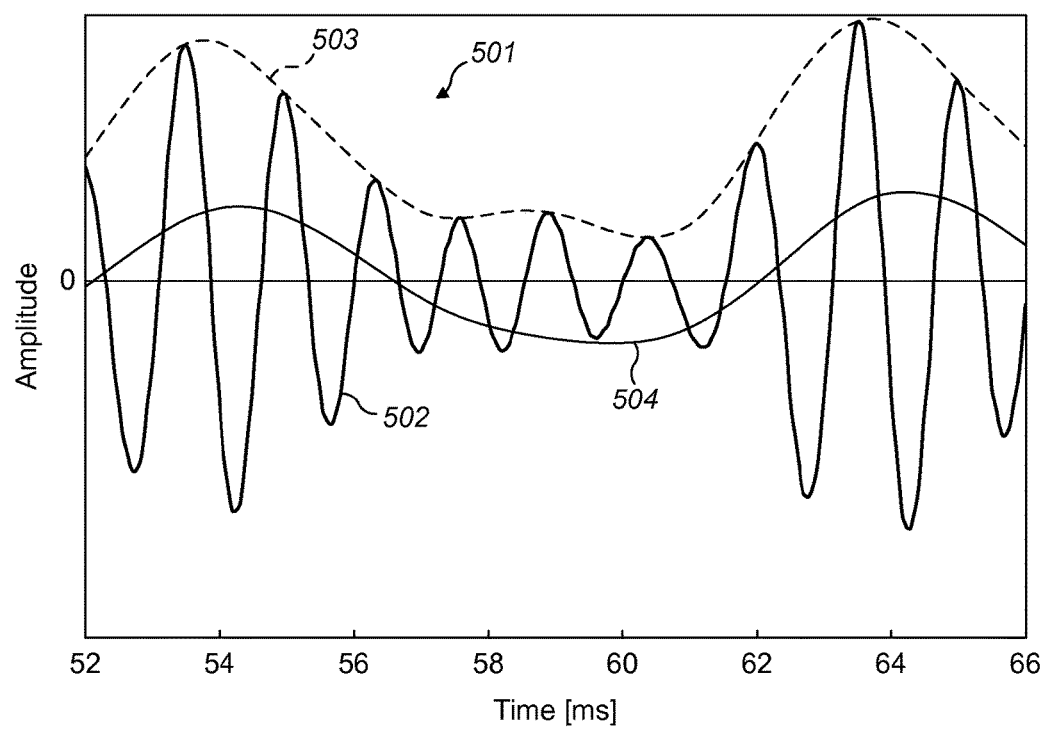
FIG. 5 shows a specific band pass signal and its various component parts.

Cochlear implant signal processing schemes typically use adaptive processing to dynamically change the band pass signal envelopes; for example, using automatic gain control (AGC), noise reduction and other dynamic signal processing stages. In addition, bilateral independent left- and right-side processing arrangements (e.g., FIG. 2) introduce temporally shifted interaural level differences (ILDs), especially during signal onsets and during changes of amplitude. But existing hearing implant signal processing arrangements also preserve interaural time differences (ITDs) in different signal components; e.g., the audio input signals, band pass signals, band pass envelopes and/or channel-specific stimulation timing pulses. The preserved ITD information can be used to modify and correct the dynamic interactions of the two sides of bilateral hearing implant systems to produce effective ILDs for a hearing implant patient that are coordinated with the corresponding signal component ITD.

Existing hearing implant systems apply only non-linear bilaterally independent signal or amplitude modifications. That permits loudness growth that is similar to normal hearing and also reduces computational effort by reducing the size of the audio data types. To maintain ILDs throughout the hearing implant system, existing processing arrangements disable any nonlinear or adaptive signal processing stages, such as AGC, noise suppression algorithms, etc. Alternatively, all non-linear and dynamic components can be bilaterally linked so that similar channel-specific or overall temporally variable gain would be applied to both left- and right-sides, though that would hamper the functioning of certain components in certain situations. For example, a noise suppression algorithm applied independently on both sides would allow reducing certain signal components in the side ipsilateral to the noise source, while at the same time maintaining channel-specific amplitudes in the contralateral system.

Figure 6:
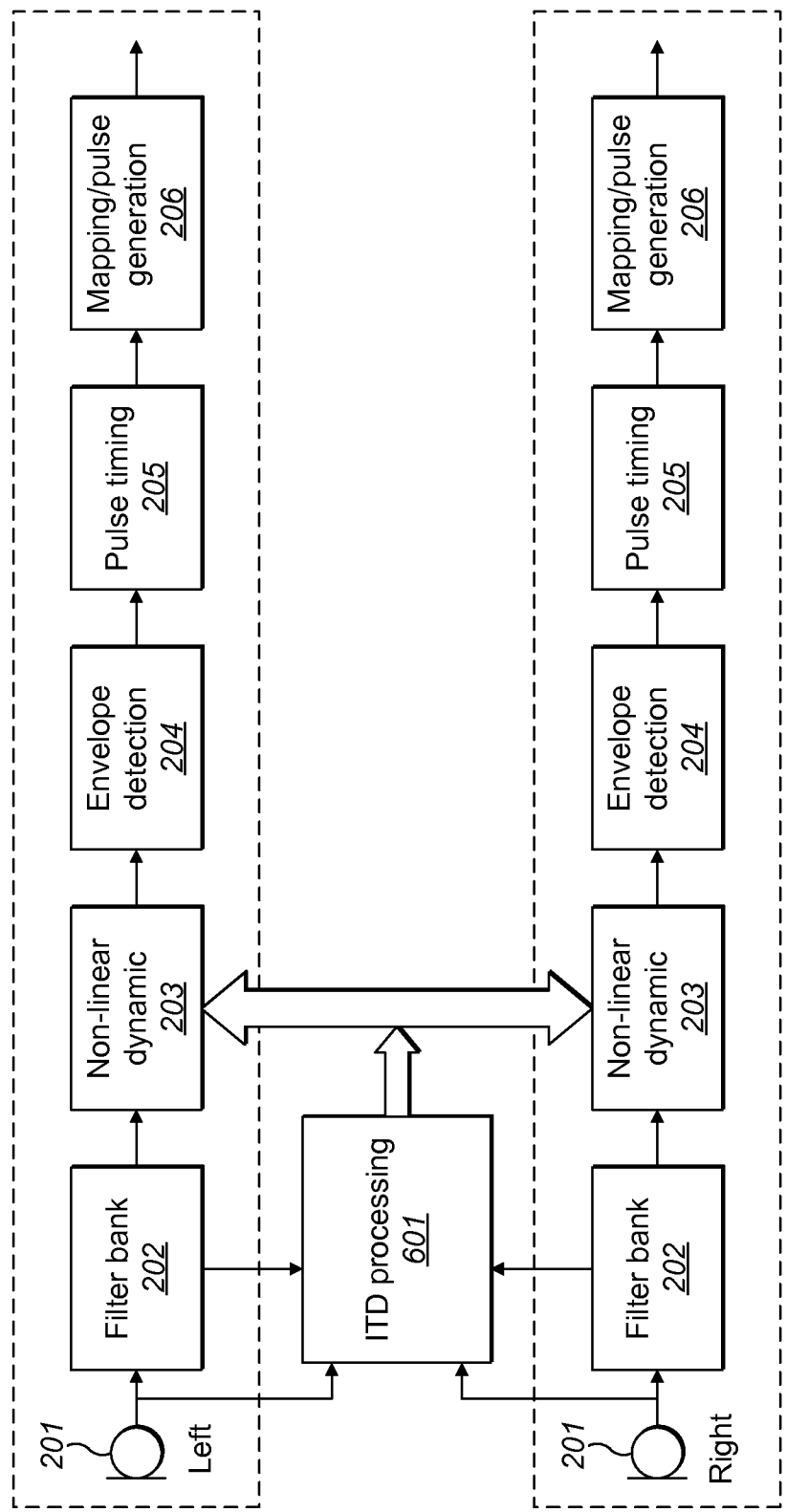
FIG. 6 shows various functional blocks in a bi-lateral cochlear implant signal processing arrangement with ITD adjusted non-linear processing stages according to one specific embodiment of the present invention.

FIG. 6 shows various functional blocks in a bi-lateral hearing implant signal processing arrangement with non-linear processing stages adjusted by channel-specific ITDs according to one specific embodiment of the present invention. Just as in existing bilateral processing arrangements, left- and right-side audio inputs are generated by sensing microphones 201 and then processed by left-side and right-side filter banks 202 that are configured to generate corresponding left-side and right-side band pass signals, where each band pass signal represents an associated band of audio frequencies in the audio input signals.

An ITD processing module 601 also receives the left- and right-side audio input signals from the sensing microphones 201 and the left- and right-side band pass signals from the left-side and right-side filter banks 202 and uses these to estimate frequency-specific ITDs. The ITD processing module 601 can receive its inputs via wireless communication means between the two left- and right-side processing paths, or from an external component capable of streaming stereo audio signals, e.g., an MP3 player, etc. In various specific embodiments, the ITD processing module 601 may be configured to estimate the ITDs using one or more of the audio input signals, the band pass signals (e.g., envelope components and/or fine structure components of the band pass signals) and/or the stimulation pulse requests to estimate the ITDs.

The ITD processing module 601 then uses the estimated ITDs to adjust channel-specific ILDs in the band pass signals as part of the non-linear/dynamic processing stage 203, which performs dynamic adjustment of the channel-specific signal components. Multiple further audio processing stages such as the envelope detection module 204, pulse timing module 205, and mapping/pulse generation module 206 then use the adjusted band pass signals from the non-linear dynamic processing module 203 to generate left-side and right-side electrode stimulation signals for the stimulation contacts in the corresponding left-side and right-side electrode arrays.

Figure 7:
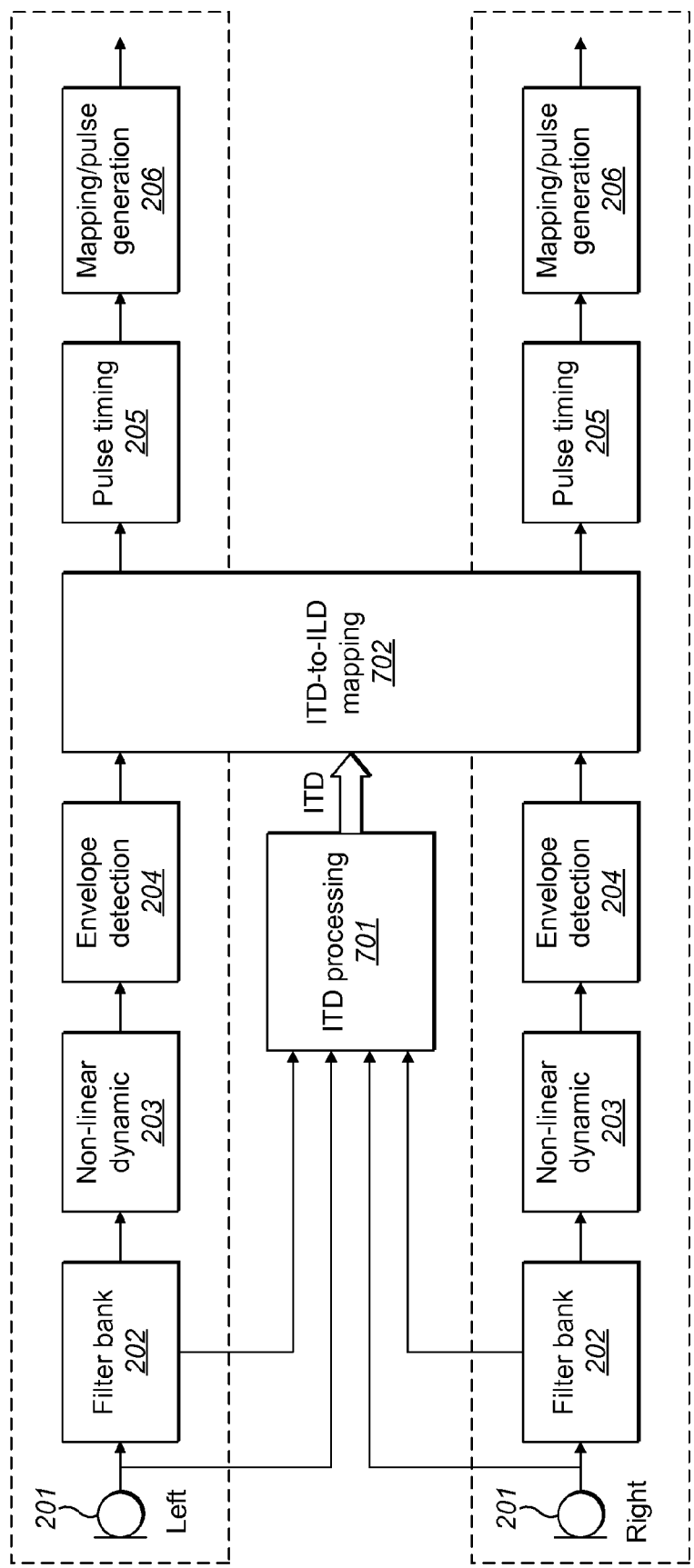
FIG. 7 shows various functional blocks in a bi-lateral cochlear implant signal processing arrangement with back-end ITD to ILD mapping according to another specific embodiment of the present invention.

FIG. 7 shows various functional blocks in a different embodiment of a bilateral hearing implant signal processing arrangement that uses back-end broadband ITD to ILD mapping. Initial processing of the left- and right-side signals is similar to existing bilateral hearing implant processing arrangements, with conventional sensing microphones 201, filter banks 202, non-linear dynamic processing module 203, and envelope detection module 204. An ITD processing module 701 receives the left- and right-side audio input signals from the sensing microphones 201 and the left- and right-side band pass signals from the left-side and right-side filter banks 202 and uses these to estimate a dominant ITD that is an output to an ITD-to-ILD mapping stage 702 that adjusts the ILDs of the signal envelopes of some or all of the channels from the envelope detection module 204. The adjusted signal envelopes are then used by the pulse timing module 205 and mapping/pulse generation module 206 to generate the electrical stimulation signals to the stimulation contacts in the implanted left- and right-side electrode arrays.

Figure 8:
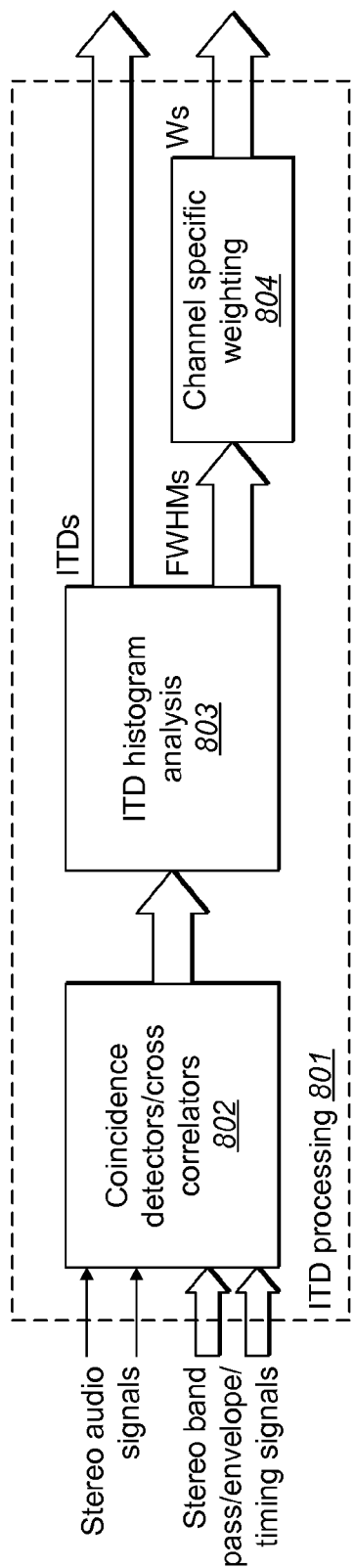
FIG. 8 shows various internal processing sub-modules in an ITD processing module using ITD histogram analysis according to another embodiment of the present invention.

An ITD Processing Module 601 or 701 can use a standard deviation of an ITD histogram to characterize accuracy of the estimated ITDs and to use a function of estimation accuracy to adjust the ILDs. FIG. 8 shows various internal processing sub-modules in an ITD Processing Module 801 that calculates an ITD histogram from overlapping measurement time windows to estimate channel-specific ITD distributions. A coincidence detector/cross correlator module 802 receives the one or more of the audio input signals, the band pass signals (e.g., envelope components and/or fine structure components of the band pass signals) and/or the stimulation pulse requests and detects the channel-specific ITDs; for example, simple implementations of models for pulse timing signals applying delay lines and coincidence detection; see Jeffress, *A Place Theory of Sound Localization*, J Comp Physiol Psychol, 41, 1947, p. 35-39, which is incorporated herein by reference. For the audio, band pass, and envelope signals, other specific techniques can be used; e.g., Lindemann, J. Acoust. Soc. Am. 80, 1608-1622 (1986) (incorporated herein by reference) or a more general cross-correlation.

Figure 9:
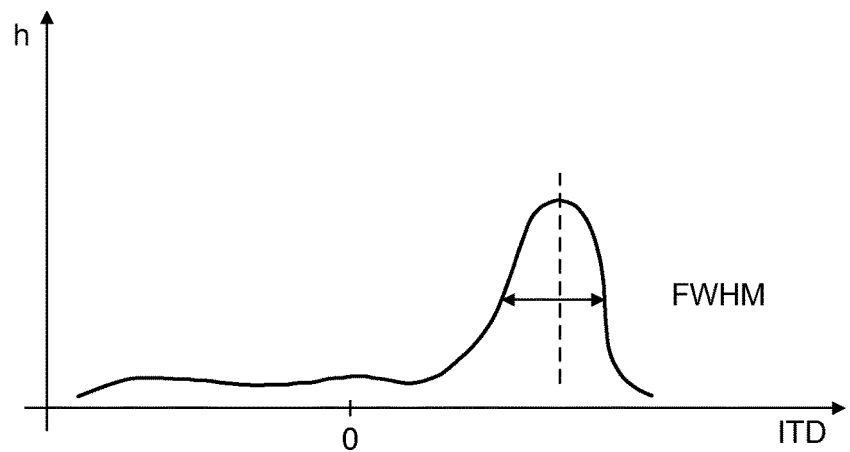
FIG. 9 shows an example of a narrow distribution ITD histogram used in one specific embodiment of the present invention.
Figure 10:
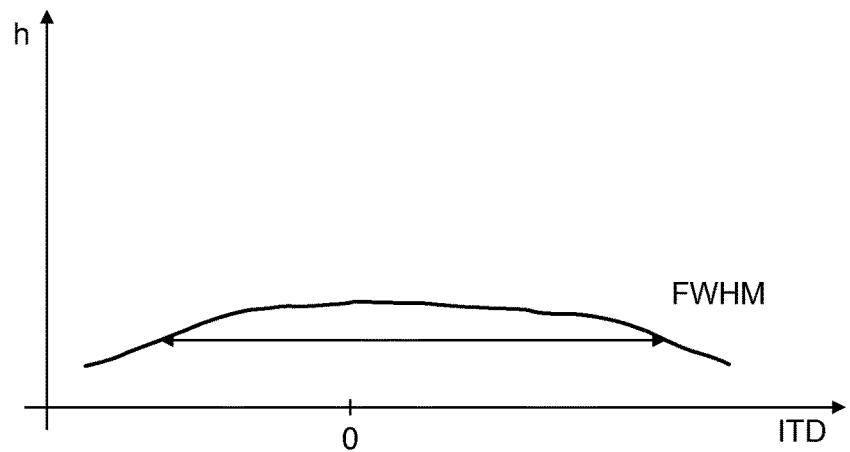
FIG. 10 shows another example of a different broad distribution ITD histogram.
Figure 11:
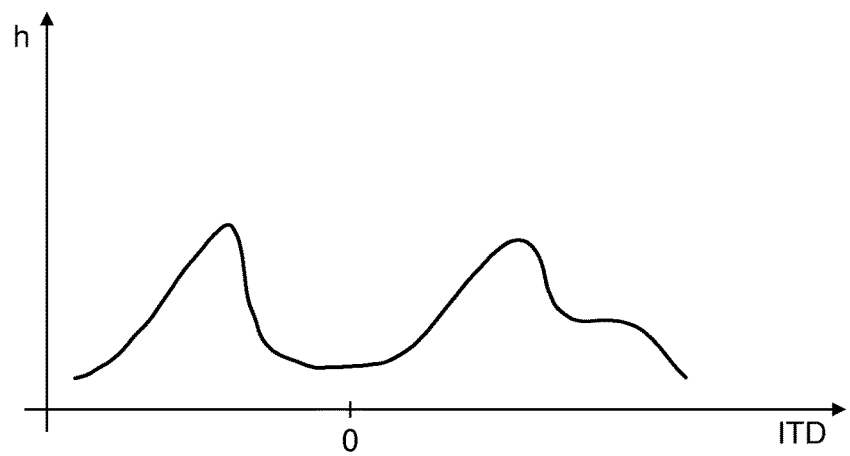
FIG. 11 shows an example of an ITD histogram with multi-modal ITD distributions.

An ITD Histogram Analysis Module 803 then uses the analyzed audio signals to dynamically modify an ITD histogram; i.e. by moving relative positions of head and sound sources or head movements. The ITD Histogram Analysis Module 803 analyzes the ITD histogram and calculates an estimate of the dominant ITD that reflects its maximum occurrence (or mean value) as well as the amount of histogram spread, which may be reflected as a full width half maximum (FWHM) value. For example, FIG. 9 shows a relatively/narrow/tight ITD histogram where the maximum/mean is shown by the vertical dashed line and the spread is characterized by a short FWHM value. FIG. 10 shows an example of a broader, more spread ITD histogram where the maximum/mean is relatively lower, while the FHWM is longer. FIG. 11 shows an example of a multi-modal ITD histogram, which leads to a high value of FWHM, which does not reflect the properties of the dominant ITD, but rather the general property of the ITD distribution.

Figure 12:
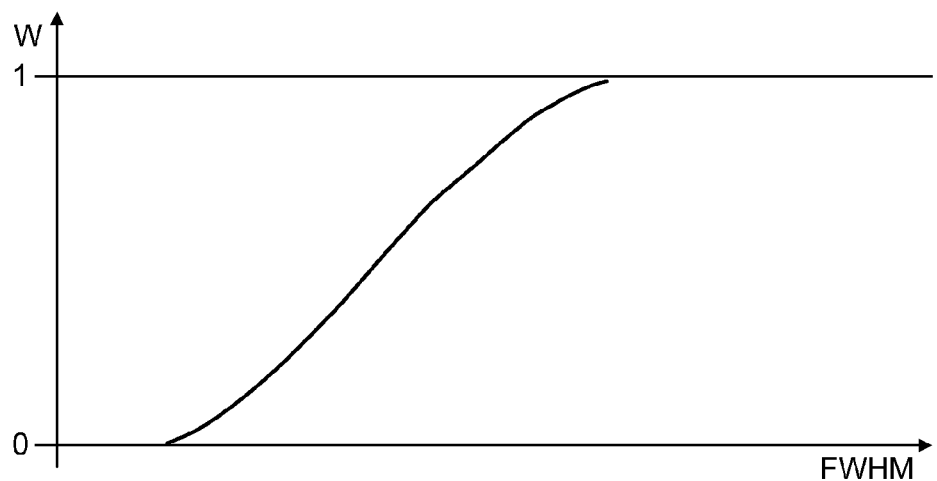
FIG. 12 shows a graph of ITD weighting factor W as a function of FWHM.

Based on the obtained quality measures of the ITD such as the FWHMs, a channel-specific weighting module 804 can calculate channel-specific weighting factors W as a function of FWHM, i.e. a logistic function as shown in FIG. 12 such that narrow ITD distributions (e.g., <100 µs) generate relatively small weighting factors W, whereas broad or multi-modal distributions (e.g., >500 µs) result in relatively large weighting factors W. The ITD information from the ITD Processing Module 801 can be used in further signal processing such as any or all of using the channel-specific weighting factors W to identify the amount of manipulation applied to band pass envelopes, applying explicit channel-specific mapping of ILDs based on the ITD information, and/or evaluating band specific ITDs and ILDs and basing ITD selection on the ILD values.

Figure 13:
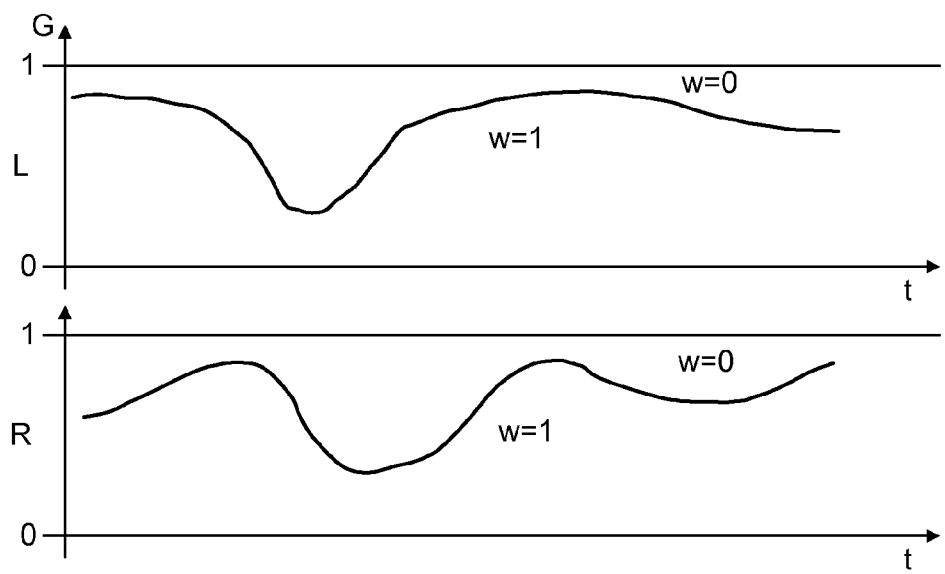
FIG. 13 shows an example of effective gains applied by a dynamic non-linear signal processing stage with channel-specific ITD weighting changing between 0 and 1.
Figure 14:
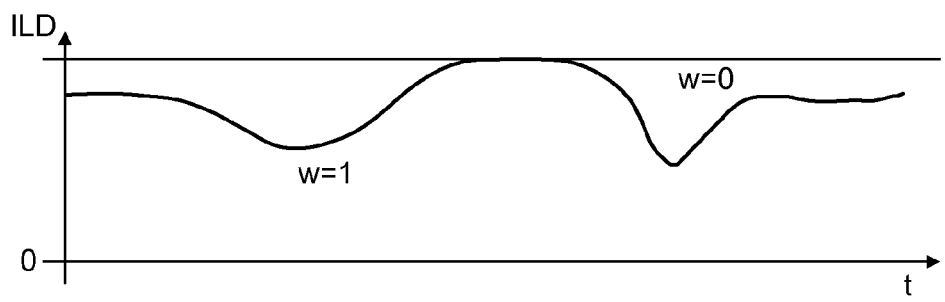
FIG. 14 shows another example of effective ILD after dynamic non-linear signal processing with channel-specific ITD weighting.

For example, the band pass signal envelopes can be modified according to the ITD weighting factors by channel specific dynamic components in the signal processing chain such as channel specific noise reduction, channel specific automatic gain controls, etc. These dynamic signal processing components perform time variant and nonlinear operations on the band pass signals, and due to the non-linear time-variant processing, the channel ILDs are not preserved since the levels L at times $t_1$ and $t_2$ are not a single linear function of the input signal x: $L(t_1,x)-L(t_1,x+a) \neq L(t_2,x)-L(t_2,x+a)$. The clearer an ITD can be detected in the channel signal or in consecutive signal components (as reflected by a small FWHM of the ITD distribution), the less change should be applied to the signal envelopes. On the other hand, a relatively large FWHM will result in W=1 (FIG. 13), and the more reliable ILDs will be retained throughout the system (FIG. 14). Therefore, clearly identifiable ITDs lead to a linearization and less time variant processing of the signal. Thus, the degree of influence of signal processing on ILDs is controlled by the quality of the measured ITD. If robust ITD are detected, the ILDs are unchanged. If ITD are scattered, the ILDs may be modified by non-linear signal processing components. The channel- or frequency-specific processing enables performing dynamic operations that preserve ILDs on those channels that provide reliable ITDs, and enhances speech understanding on those channels who do not provide reliable ITDs. And so a balance of speech understanding and ILD transmission is achieved.

Some embodiments of the invention can apply a universal weighting factor (one on each side of a bilateral system) to the broadband nonlinear dynamic components of the system (e.g. AGC). This may be based on determining dominant ITDs the ITD analysis stage. From the n ITDs that are calculated from the n filter bands, the dominant ITD with the smallest FWHM can be selected to calculate a universal broadband weighting factor $W_u$: $W_u=W(i)$, where FWHM (i)<FWHM(n≠i). Alternatively, a universal weighting factor can be computed from a distribution function such as the mean value of the channel specific weighting factors: $W_u=\text{mean}(W(i))$. Or the ITD from the channel with the best signal to noise ratio (SNR) can be chosen for calculation of the universal weighting function (as noise will disturb the target signals (speaker) ITD).

Figure 15:
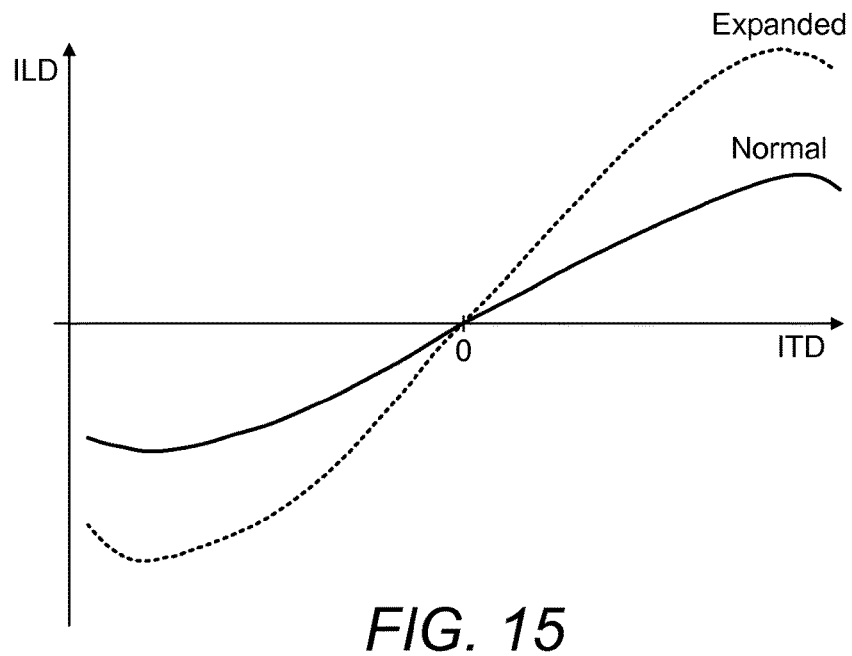
FIG. 15 shows an example of two different pre-defined channel-specific ITD-to-ILD mapping functions.
Figure 16:
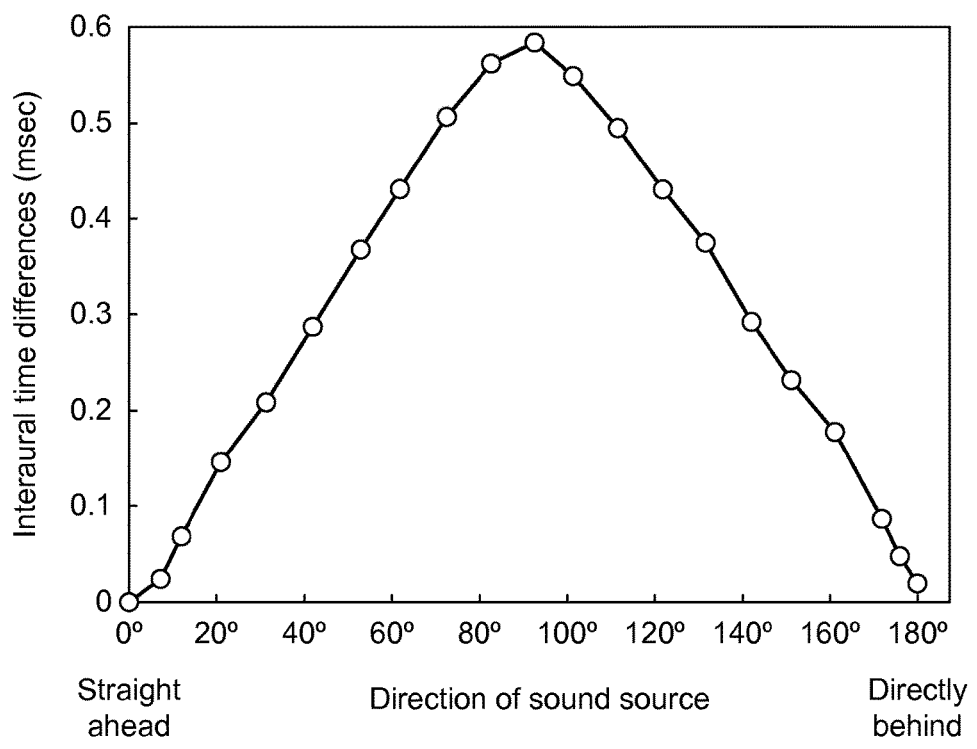
FIG. 16 shows an example of ITD-to-ILD mapping reflecting direction angle of the target sound source.

Estimated ITDs also can be used to directly map to channel-specific ILDs in a system such as the one shown in FIG. 7 with an ITD-to-ILD mapping stage. The ITD is estimated from the maximum/mean of the ITD histogram, a dominant ITD is determined from n ITDs as described above, and a desired ILD can be stored in a pre-defined channel specific mapping function in the mapping stage as shown, for example, by FIG. 15. The ITD-to-ILD mapping functions can be derived, for example, from head related transfer functions that can be derived from a KEMAR manikin. For the ITD to ILD mapping, the direction angle Θ of the target sound source can be estimated with the dominant ITD, and with that direction angle, the appropriate HRTF(Θ) can be selected. The ILD is computed with ILD only HRTF_ILD(Θ) that can be derived from HRTF(Θ) by using identical phase responses for both ears. If X and Y are the Fourier transform of the input signal x and output signal y, then this can be written as: Y=X*HRTF_ILD(Θ), with Θ as a function of ITD as shown in FIG. 16. ILD as a function of ITD can also be exaggerated as indicated by the "Expanded" line in FIG. 15 where the smaller of the bilateral envelope is changed according to match the desired ILD value.

The ILD manipulation can be triggered by the FWHM of the ITDs, meaning that ILD manipulation is only performed if the FWHM lies below a defined threshold. Thus, in presence of a robust channel specific ITD, the output ILD is aligned to the measured ITD, whereas a sluggish ITD (reflected by a high w) result in no change of the signal envelopes. This one ITD is then used to compute a universal weighting function for all channels, resulting in an unambiguous ILD over all channels. Fixed band specific weights can be applied additionally to account for frequency-specific ILD variations.

Even in the presence of a single spatially stationary sound source such as a human voice, existing hearing implant systems modify ILDs while ITDs remain relatively constant. But embodiments of the present invention allow control over time of signal components which modify ILDs in order to deliver coordinated ITDs and ILDs to a bilateral hearing implant patient. Such a system can set the ILDs naturally, and extend or decrease them. This also allows balancing the relative contribution of ITDs and ILDs on lateralization of a sound percept based on patient-specific sensitivities to the two features.

For example, a 600 µs ITD present in the stimulus might generate a full lateralization. In the same bilateral pair of channels, an ILD of 10 dB might generate full lateralization, whereas the maximum ILD available in the acoustic might only be 3 dB. In that case, the ILD can be mapped to a range of −10 dB to +10 dB over a the physiologic range of ITDs. As a system identifies the quality of detected ITD and sets the amount of influence on ILDs, misinterpretations are very unlikely because ITDs and ILDs get matched only if a single sound source is detected. ILDs produced by such a system can be more easily interpreted by the hearing implant user since they are (like in normal hearing) very well-related to the ITDs, and a conflict between inconsistent ITDs and ILDs could be removed or reduced.

Embodiments of the invention may be implemented in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for auditory prostheses other than cochlear implants such as an auditory brainstem implant with the electrical stimuli presented by electrodes within or adjacent to the cochlear nucleus, or an auditory midbrain implant with the electrical stimuli presented by electrodes on or within the inferior colliculus. In addition, corresponding methods and systems may also be used for deep brain stimulation.

What is claimed is:

1. A bilateral hearing implant system comprising:
   implanted left-side and right-side electrode arrays, each with a plurality of stimulation contacts for delivering electrode stimulation signals to adjacent auditory neural tissue;
   left- and right-side filter banks configured to process left- and right-side audio input signals to generate corresponding left- and right-side pluralities of band pass signals, wherein each band pass signal represents an associated band of audio frequencies in the audio input signal;
   an interaural time delay (ITD) processing module configured to:
      i. estimate ITDs for the band pass signals by calculating an ITD histogram from overlapping measurement time windows,
      ii. determine a standard deviation of the ITD histogram to characterize accuracy of the estimated ITDs, and
      iii. use the estimated ITDs as a function of estimation accuracy to adjust interaural level differences (ILDs) in the band pass signals; and
   a plurality of audio processing stages configured to use the adjusted band pass signals to generate left-side and right-side electrode stimulation signals for the stimulation contacts in the corresponding left-side and right-side electrode arrays.

2. The system according to claim 1, wherein the ITD processing module is configured to use the audio input signals to estimate the ITDs.

3. The system according to claim 1, wherein the ITD processing module is configured to use the band pass signals to estimate the ITDs.

4. The system according to claim 3, wherein the ITD processing module is configured to use envelope components of the band pass signals to estimate the ITDs.

5. The system according to claim 3, wherein the ITD processing module is configured to use fine structure components of the band pass signals to estimate the ITDs.

6. The system according to claim 1, wherein the ITD processing module is configured to use stimulation pulse requests to estimate the ITDs.

7. The system according to claim 1, wherein the ITD processing module adjusts channel-specific ILDs of the band pass signals.

8. The system according to claim 1, wherein the ITD processing module adjusts broadband ILDs of the band pass signals.

9. The system according to claim 1, wherein the ITD processing module adjusts channel-specific dynamic components in the signals.

10. The system according to claim 1, wherein the ITD processing module is configured to use an estimation accuracy threshold to determine when to adjust the ILDs such that an ILD is adjusted when estimation accuracy of the corresponding ITD is less than the estimation accuracy threshold, but the ILD is not adjusted when estimation accuracy of the corresponding ITD is greater than the estimation accuracy threshold.

11. A method of generating electrode stimulation signals for stimulation contacts in implanted electrode arrays of a bilateral hearing implant system having a left-side electrode array and a right-side electrode array, the method comprising:

processing left-side and right-side audio input signals to generate corresponding left-side and right-side pluralities of band pass signals, wherein each band pass signal represents an associated band of audio frequencies in the audio input signal;

estimating frequency-specific interaural time delays (ITDs) for the band pass signals by calculating an ITD histogram from overlapping measurement time windows;

determining a standard deviation of the ITD histogram to characterize accuracy of the estimated ITDs;

using the estimated ITDs as a function of estimation accuracy to adjust interaural level differences (ILDs) in the band pass signals; and using the adjusted band pass signals to generate left-side and right-side electrode stimulation signals for the stimulation contacts in the corresponding left-side and right-side electrode arrays.

12. The method according to claim 11, wherein the audio input signals are used for estimating the ITDs.

13. The method according to claim 11, wherein the band pass signals are used for estimating the ITDs.

14. The method according to claim 13, wherein envelope components of the band pass signals are used for estimating the ITDs.

15. The method according to claim 13, wherein fine structure components of the band pass signals are used for estimating the ITDs.

16. The method according to claim 11, wherein stimulation pulse requests are used for estimating the ITDs.

17. The method according to claim 11, wherein the adjusted ILDs are channel-specific ILDs.

18. The method according to claim 11, wherein the adjusted ILDs are broadband ILDs.

19. The method according to claim 11, wherein adjusting ILDs in the band pass signals includes adjusting channel-specific dynamic components in the signals.

20. The method according to claim 11, wherein an estimation accuracy threshold is used to determine when to adjust the ILDs such that an ILD is adjusted when estimation accuracy of the corresponding ITD is less than the estimation accuracy threshold, but the ILD is not adjusted when estimation accuracy of the corresponding ITD is greater than the estimation accuracy threshold.

* * * * *